(12) United States Patent
Angle

(10) Patent No.: US 10,034,908 B2
(45) Date of Patent: Jul. 31, 2018

(54) TREATMENT OF VIRUS-BASED DISEASES OF THE SKIN

(71) Applicant: COUNTERPOINT HEALTH SOLUTIONS, INC., Bedford, MA (US)

(72) Inventor: Erika N. Angle, Bedford, MA (US)

(73) Assignee: IXCELA, INC., Bedford, MA (US)

( * ) Notice: Subject to any disclaimer, the term of this patent is extended or adjusted under 35 U.S.C. 154(b) by 0 days.

(21) Appl. No.: 14/737,164

(22) Filed: Jun. 11, 2015

(65) Prior Publication Data

US 2015/0359833 A1    Dec. 17, 2015

Related U.S. Application Data

(60) Provisional application No. 62/010,860, filed on Jun. 11, 2014.

(51) Int. Cl.
| | | |
|---|---|---|
| *A61K 36/00* | (2006.01) | |
| *A61K 36/288* | (2006.01) | |
| *A61K 31/4196* | (2006.01) | |
| *A61K 31/7076* | (2006.01) | |
| *A61K 9/00* | (2006.01) | |

(52) U.S. Cl.
CPC .......... *A61K 36/288* (2013.01); *A61K 9/0014* (2013.01); *A61K 31/4196* (2013.01); *A61K 31/7076* (2013.01)

(58) Field of Classification Search
CPC ...................................................... A61K 36/00
USPC ....................................................... 424/725
See application file for complete search history.

(56) References Cited

U.S. PATENT DOCUMENTS

2012/0269912 A1    10/2012    Roberts ................. 424/736

FOREIGN PATENT DOCUMENTS

| | | | | |
|---|---|---|---|---|
| CN | 101023972 | | 8/2007 | ........... A61K 36/288 |
| CN | 101391044 | * | 3/2009 | |
| CN | 101181366 | * | 6/2010 | |
| CN | 102068611 | | 5/2011 | ........... A61K 36/898 |
| CN | 103800485 | | 5/2014 | ............. A61K 36/74 |

OTHER PUBLICATIONS

Herpes Simplex, 5 pages, 2017.*
Database Medline (online) US National Library of Medicine (NLM), Bethesda, MD, US, Jan. 1990, Zheng M: "[Experimental study of 472 herbs with antiviral action against the herpes simplex virus]." XP002776231, abstract only, 1 pg, ISSN: 0254-0934.
Database Embase (online) Elsevier Science Publishers, Amsterdam, NL; 1959, Tuan F-T: "Herpes zoster treated by traditional Chinese drugs", XP002776232, abstract only, 1 pg. ISSN: 0412-4030.
Extended European Search Report issued in corresponding EPO Patent Appln. Serial No. 15807542.4-1112 dated Jan. 9, 2018, 8 pgs.
International Search Report and Written Opinion issued in application No. PCT/US15/35384, dated Sep. 11, 2015 (9 pgs).
Chaudhary et al., 'Ethnobotany of Medicinal Plants from Tian Mu Shan Biosphere Reserve, Zhejiang-Province, China'. Asian Journal of Plant Sciences, 2006, vol. 5, issue 4, pp. 646-653 (8 pgs).
Schultz et al., 'Taraxacum—A review on its phytochemical and pharmacological profile'. Journal of Ethnopharmacology, 2006, vol. 107, pp. 313-323 (11 pgs).

* cited by examiner

*Primary Examiner* — Michael V Meller
(74) *Attorney, Agent, or Firm* — Hayes Soloway P.C.

(57) ABSTRACT

A method for treatment of virus-based diseases of the skin, in particular, herpes simplex virus type-1 and herpes zoster, which comprises topically administering to the skin of a subject suffering from a virus-based disease of the skin a therapeutically amount of an aqueous, aqueous/alcohol, or natural plant oil extract of dandelion.

3 Claims, 8 Drawing Sheets

TREATMENT OF VIRUS-BASED DISEASES OF THE SKIN

CROSS REFERENCE TO RELATED APPLICATION

This application claims priority from U.S. Provisional Application Ser. No. 62/010,860, filed Jun. 11, 2014, the contents of which are incorporated herein by reference.

FIELD OF THE INVENTION

The present invention relates to the treatment of certain virus-based diseases of the skin, in particular for the treatment of herpes simplex virus type-1 (HSV-1) and herpes zoster, commonly known as shingles or varicella zoster virus (VZV).

BACKGROUND OF THE INVENTION

Virus-based diseases of the skin include in particular diseases and/or infections which are caused by herpes viruses and are also referred to colloquially simply as herpes. Herpes viruses occur widely in vertebrates, in particular in mammals and especially in humans, horses, swine, cattle, goats, sheep, cats and dogs.

Human pathogenic herpes viruses (HHV) are differentiated according to alpha, beta, and gamma-herpes viruses (HHV-1 through HHV-8), where the alpha and gamma viruses are also among viruses that can infect animals, e.g., the horse (equine herpes virus), cattle (bovine herpes virus), swine (porcine herpes virus), cat (feline herpes virus), dog (canine herpes virus) and chicken (chicken herpes virus 1).

Of the human pathogenic herpes viruses, those which infect humans, in particular the alpha-herpes viruses, are of great importance. The alpha-herpes viruses include herpes simplex virus 1 (HSV-1), herpes simplex virus 2 (HSV-2) and varicella zoster virus (VZV).

The diseases of the skin caused by herpes simplex viruses HSV-1 and HSV-2 include, for example, herpes labiales, also known as fever blisters or herpes of the lips, and herpes nasalis, both caused primarily by HSV-1, keratoconjunctivitis herpetica, stomatitis herpetica, herpes facialis, herpes buccalis, herpes genitales, herpes perianalis, herpes gluteaiis. Varicella zoster viruses (VZV) cause chickenpox and shingles, for example.

Virologists have estimated that 80% of the population worldwide has latent HSV-1 infections and 30% HSV-2. HSV-1 and HSV-2 are closely related to one another and have a high percentage of identical nucleotide sequences. Although HSV-1 infects primarily the oral and facial area, HSV-2 occurs mainly in the genital area.

Alpha-herpes viruses usually first infect epithelial cells such as skin cells, mucous cells and mucosal cells, followed by a marked replication of the virus in the host cell and death of the infected host cell.

For example, HSV-1 will spread in skin cells and/or mucosal cells of the face and mouth, usually causing local damage, namely in the form of a vesicle. Antibodies neutralize the viruses in the vesicles after a short period of time, but viruses are also released by lysis of the infected host cells before a humoral immune response can take place. The viruses thereby released also infect certain nerve cells (neurons) by adhering to receptors on the nerve endings in the mouth, which can lead to the neural node of the facial nerve (trigeminus). The viral DNA penetrates into an axon, enters the cytoplasm of the nerve cells and finally enters the cell nucleus where the viral DNA is incorporated into the genome of the nerve cell, leading to a latency in which only a few viral genes are expressed (lysogenic cycle). Various external stimuli can be lead to renewed activation of the virus, i.e., the transition from latency and/or the lysogenic cycle to the lytic cycle which ultimately results in destruction (lysis) of the nerve cell. Such stimuli include, for example, immunosuppression, stress, hormone fluctuations, physical or emotional stresses, fever (which is also why they are called fever blisters), UV radiation, tissue damage and in many cases an immunological weakness. The incidence of such activation of HSV-1 is believed to depend on both genetic and environmental factors, and both age and hormone changes can play a role. The viral progeny occurring as part of an activation are first transported by the axon to the site and/or region of the original skin infection where they again create vesicles or blisters (fever blisters) by infection of and replication in the skin cells and/or mucosal cells. Even if these viruses are again neutralized by the immune system, it is impossible to free the body completely of HSV-1 through the immune system because additional nerve cells in which the viral DNA remains integrated into the genome (latency) are constantly being infected.

Herpes virus-based diseases of the skin are generally treated by using antiviral active ingredients which intervene in viral replication in particular, as will be discussed in greater detail below.

An important general approach in the development of antiviral active ingredients and thus also in the prevention and/or treatment of virus-based diseases of the skin is thus to intervene in the viral replication cycle and to inhibit viral infection of the host cell or replication of the viral nucleic acid in the host cell, e.g., by inhibiting expression of the viral proteins coded by the viral nucleic acid.

In recent decades, such antiviral active ingredients, so-called virustatics have been developed. Many virustatics inhibit the enzyme DNA polymerase, reverse transcriptase or proteases, for example, and thus inhibit replication of the virus and/or processing of a synthesized long virus protein into smaller protein segments. Examples of these therapeutic approaches are to be found here in particular in the treatment of HIV infections. However, virustatics that are administered systemically or topically are also known in the field of treatment of virus-based diseases of the skin caused by herpes viruses HSV-1 or HSV-2. Examples include the active ingredients aciclovir, valaciclovir, foscarnet and penciclovir.

In general two approaches are known for prevention and/or treatment of virus-based diseases of the skin with virustatics: (1) systemic administration: by systemic administration of virustatics, a significant reduction in the activation of viruses present in host cells can be achieved because the active ingredients inhibit the replication of the viral nucleic acid in the cell nucleus or the assembly of the viral particles to form complete viruses in the cytoplasm of the host cells; (2) topical administration: by topical administration of virustatics in the area of an initial infection by the virus, the additional route of replication of the viruses, e.g., in the resulting fever blisters in the case of an HSV-1 infection, can be prevented in an early stage of activation, which can result in more rapid detumescence of the fever blisters.

Both approaches have some important disadvantages for administration of virustatics: In systemic administration, the dose required for effective treatment is relatively high and is associated with serious adverse effects for the organism thereby treated such as, for example, nonspecific immune responses and autoimmune responses. In the case of aciclovir, numerous such adverse effects are known from the literature. Therefore, neither long-term treatment nor repeat treatment is advisable nor can it be expected of a patient. In topical administration, the amount of active ingredient (virustatic) that can be released and be bioavailable per unit of time in the area of the virus infection, e.g., the fever blister is very low. This low bioavailability of the virustatic is an important obstacle for effective topical treatment. In the case of aciclovir which has a very low water solubility, the low bioavailability is due to the poor percutaneous transport of the active ingredient, for example. Various chemical modifications of virustatics as prodrug concepts for an improved supply of virustatic active ingredient have not led to any improvement in this phenomenon.

The foregoing discussion of the prior art derives primarily from U.S. Pat. No. 8,609,147 in which there is proposed use of deuterium oxide for treating herpes virus-based disease of the skin by topically administering deuterium oxide to the skin of a subject suffering from a herpes virus-based disease.

SUMMARY OF THE INVENTION

The present invention provides an alternative and improved method for treatment of herpes virus-based diseases of the skin. More particularly, I have found aqueous and aqueous/alcohol extracts of dandelion greens, leaves and roots unexpectedly may be used as a topical treatment for treating herpes simplex virus type-1 (HSV-1) and herpes zoster (VZV).

More particularly, I have found that aqueous, aqueous/alcohol, and natural plant oil extracts of dandelion unexpectedly provide relief for both herpes simplex and herpes zoster when applied topically.

BRIEF DESCRIPTION OF THE DRAWINGS

Further features and advantages of the present invention will be seen from the following detailed description taken in conjunction with the accompanied drawings, wherein.

DETAILED DESCRIPTION

As used herein "alcohol" means a lower, preferably $C_1$ to $C_4$, alcohol. And, natural plant oil means flax oil, which is preferred, or another commercially available oil such as almond oil, coconut oil, jojoba oil, lemon oil, olive oil, sesame seed oil and sunflower oil, which are given as examples.

Preparation and Extraction Protocol Dried dandelions (country of origin Mongolia) were chopped and extracted by boiling either in distilled water or methanol (50 g of dandelion to 1250 mL of water or methanol). The DI water and alcohol extracts were tested on the HSV-1 by leaving various dilutions ranging from 1:1, 1:2, 1:5, 1:10 in contact with the virus for 30 minutes, then pipetting off the extract. The virus was then pipetted into a tube of MRC-5 cells and the tubes observed for cytopathic effect. Concentrations of 1:1 and 1:2 of the TM extracts prevented viral proliferation.

In the case of shingles, the plants were prepared in similar fashion, but only in DI water. Individuals diagnosed with shingles saturated a towel with liquid TM extract and applied the material with a towel to their bodies for 20 minutes at a time every two hours or as needed. They did this for a day or two as needed. Within two days the shingles were gone.

Figure 8:
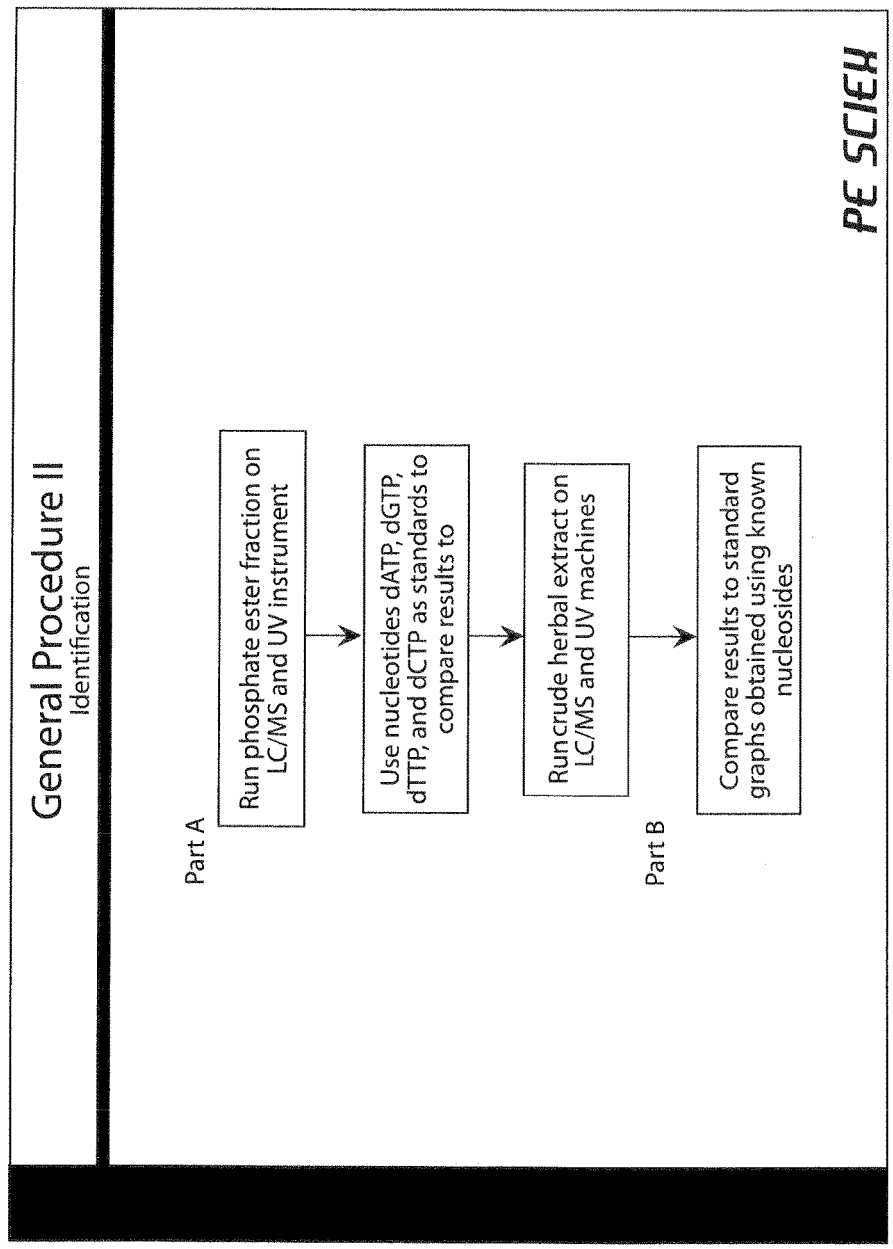
FIG. 8 is a flow diagram of a general identification procedure used in the present invention.

The extract was removed and fractionated on an LC/MS and UV instrument following the general procedure set forth in FIG. 8. DI water extracts that had been analyzed using LC/MS/MS were then tested on HSV-1 (same dilutions as above) by leaving the various dilutions in contact with the virus for 30 minutes and then pipetting the solutions into test tubes containing MRC-5 cells. The tubes were observed for cytopathic effect (CPE).

Figure 1:
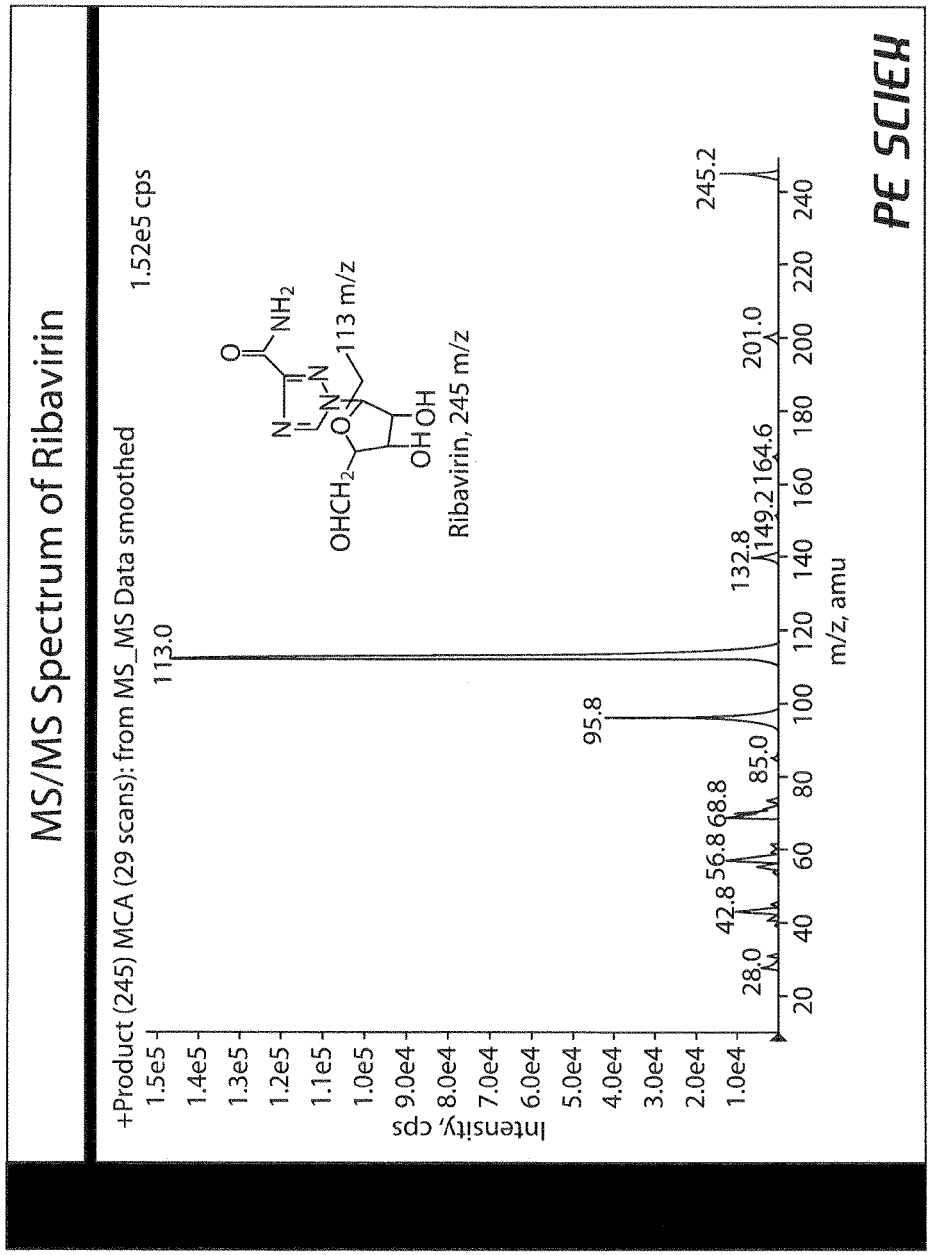
FIGS. 1-3 are MS/MS spectra of known nucleoside analogs.
Figure 2:
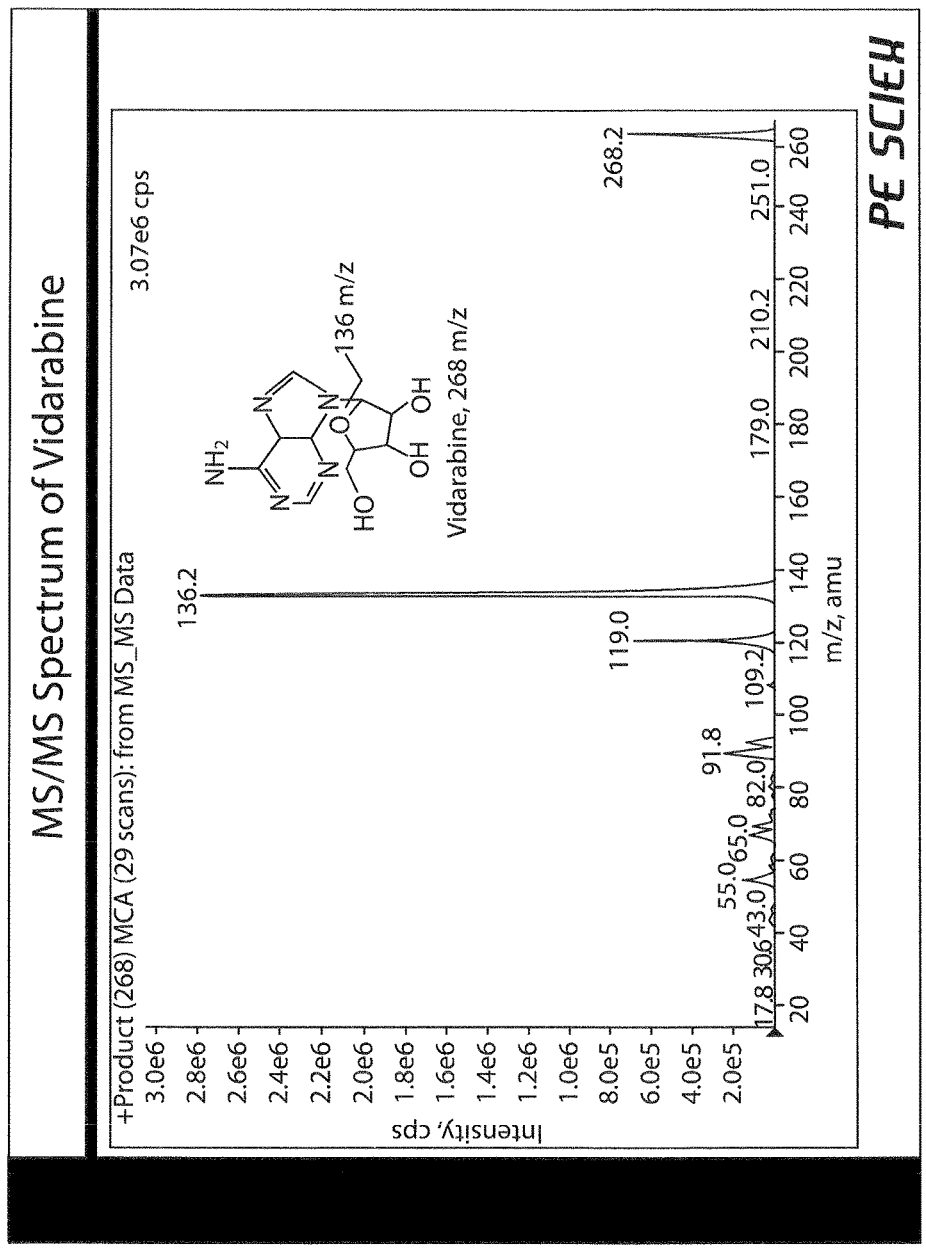
Figure 3:
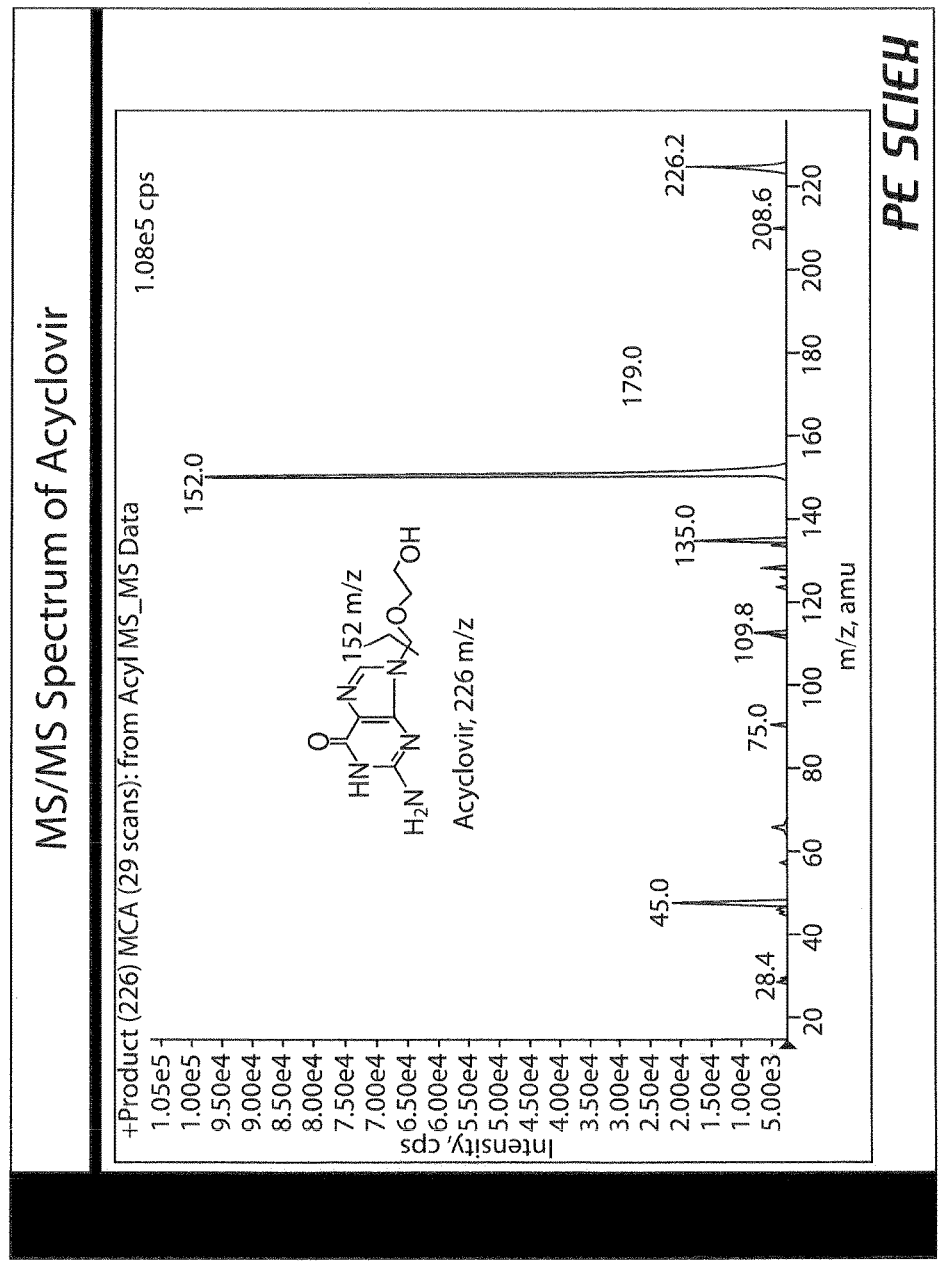
Figure 4:
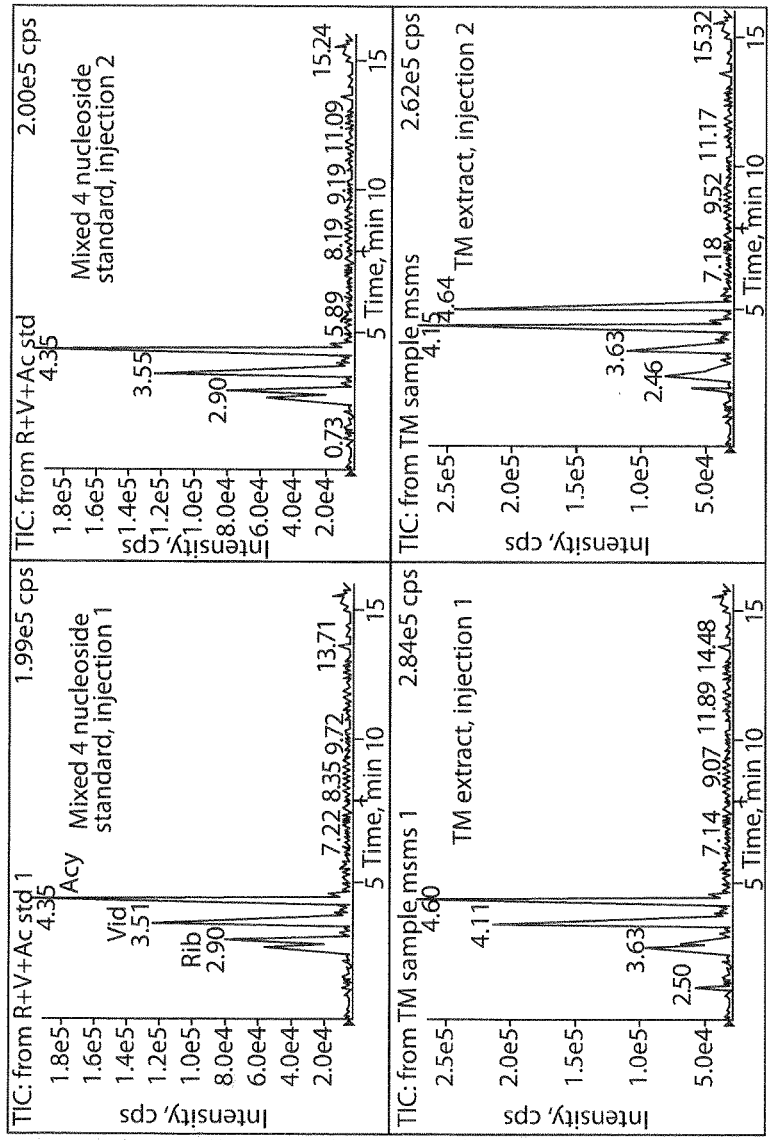
FIG. 4 is an LC/MS/MS analysis of nucleoside standards and nucleosides found in *T. mongolicum* extract.
Figure 5:
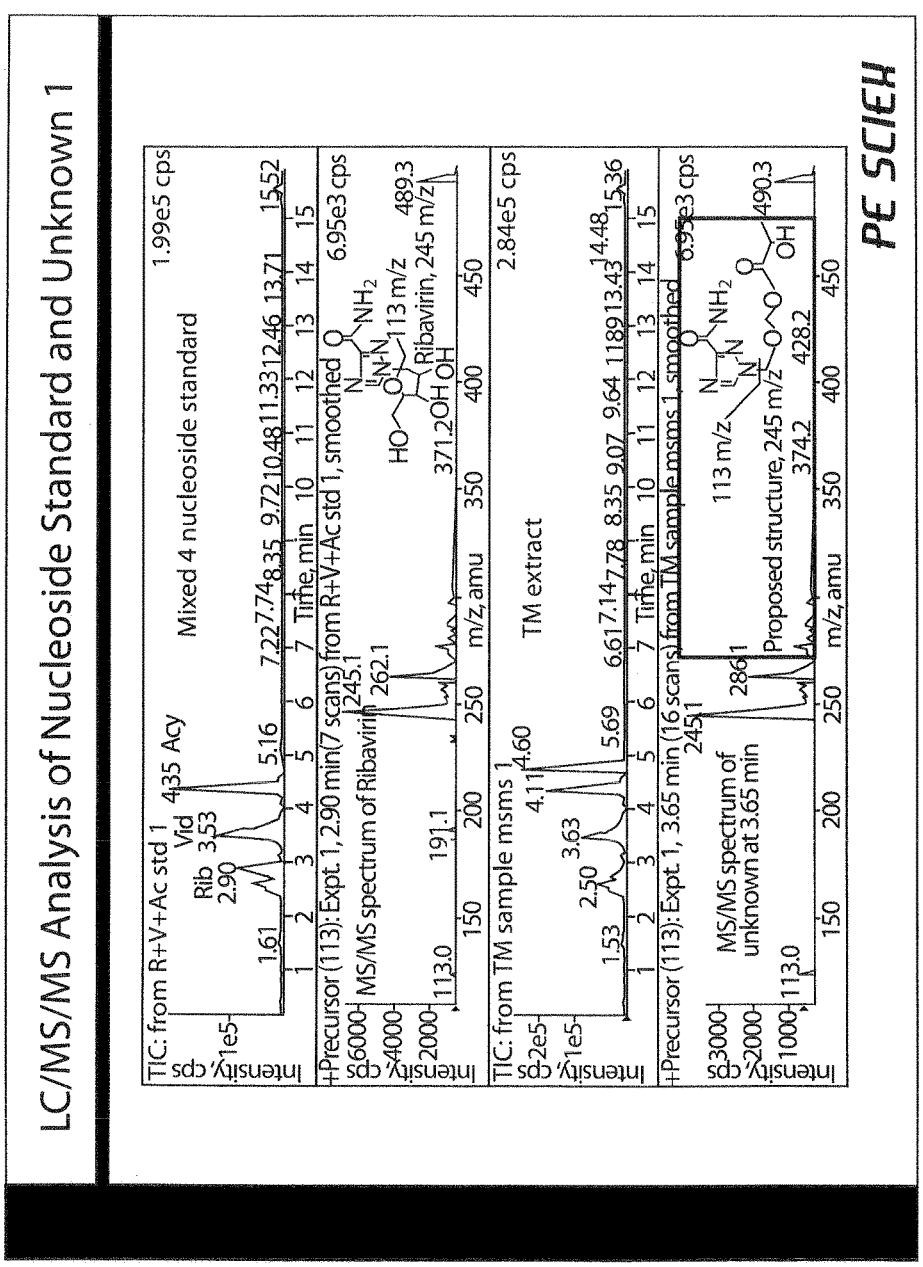
FIGS. 5-7 are LC/MS/MS analysis comparing known nucleosides to those novel nucleoside analogs found in *T. Mongolicum*. Novel nucleoside structures proposed are circled in red.
Figure 6:
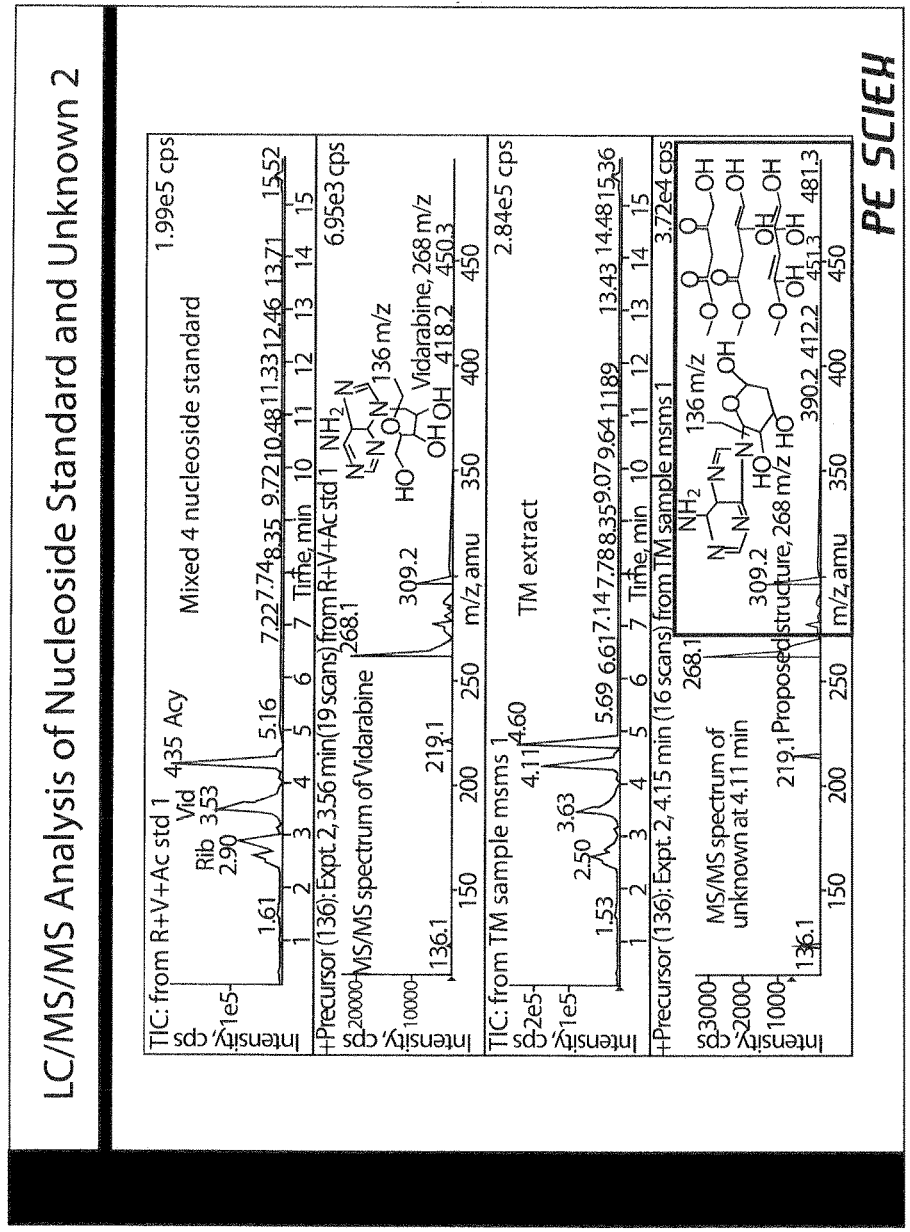
Figure 7:
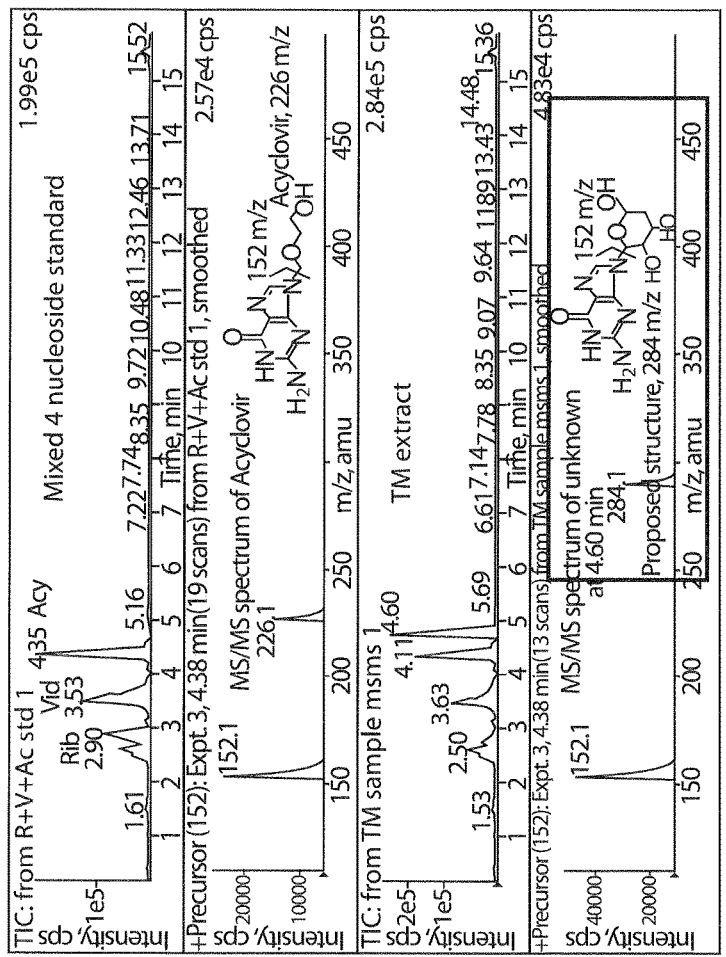

Similar results were seen with different batches of Mongolian dandelion and different extraction solutions, including oils, validating reproducibility of results. While not wishing to be bound by theory, it is believed certain nucleosides contained in dandelion extracts may contribute more to the effects observed. These compounds were isolated and their proposed structures identified in FIGS. 5-7. Notwithstanding, other components of the extract also may play a role.

The invention claimed is:

1. A method for treating herpes simplex virus type-1 in a human in need thereof consisting essentially of topically administering to the skin of the human in need thereof a therapeutically effective amount of an aqueous or aqueous/alcohol extract of Mongolian dandelion and an oil selected from the group consisting of flax oil, almond oil, coconut oil, jojoba oil, lemon oil, olive oil, sesame seed oil, and sunflower oil, wherein the extract of Mongolian dandelion is prepared by boiling.

2. The method of claim 1, wherein the extract of Mongolian dandelion is an aqueous/alcohol extract.

3. The method of claim 1, wherein the extract of Mongolian dandelion consists of the following structure:

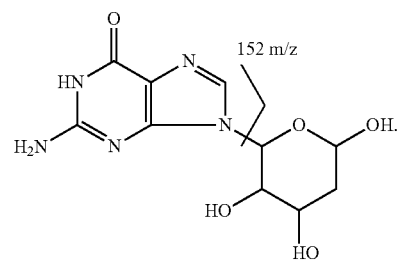 [SMILES: Nc1nc2c(ncn2C2OC(O)CC(O)C2O)c(=O)[nH]1]

* * * * *